United States Patent [19]
Dellinger

[11] Patent Number: 4,657,508
[45] Date of Patent: Apr. 14, 1987

[54] ORTHODONTIC APPARATUS AND METHOD FOR TREATING MALOCCLUSION

[76] Inventor: Eugene L. Dellinger, Fort Wayne, Ind.

[21] Appl. No.: 728,856

[22] Filed: Apr. 30, 1985

Related U.S. Application Data

[63] Continuation-in-part of Ser. No. 562,858, Dec. 19, 1983, Pat. No. 4,526,540, and a continuation-in-part of Ser. No. 662,727, Oct. 19, 1984, Pat. No. 4,551,096.

[51] Int. Cl.$^4$ ................................................ A61C 7/00
[52] U.S. Cl. ............................................ 433/24; 433/9
[58] Field of Search ..................... 433/3, 8, 9, 16, 26

[56] References Cited

U.S. PATENT DOCUMENTS

| | | | |
|---|---|---|---|
| 1,426,802 | 8/1922 | Woodward | 411/366 |
| 1,711,453 | 4/1929 | Carr | 411/366 |
| 3,969,821 | 7/1976 | Lee et al. | 433/9 |

*Primary Examiner*—Robert Peshock
*Attorney, Agent, or Firm*—Pearne, Gordon, McCoy & Granger

[57] ABSTRACT

The invention comprehends the use of a bracket having a non-conforming base portion, mountable to a tooth in a preestablished position and angular orientation through the formation of an associated contoured shim, and a head portion symmetrically opposite to the base portion, the head portion having a slot therein adapted and oriented to receive a conventional dental arch wire. A fixture is formed to fit over a tooth replica on which a bracket and shim is affixed, this fixture having an internal cavity which matches the shape and contour of the tooth, such as lingual surface, incisal edge and the labial surface, and includes the head portion of the bracket so as to align the conforming surface of the contoured shim with the same anatomical tooth surface as the labial or lingual surface matched by the fixture. The contoured shim formed to surround the non-conforming surface of the base of the bracket completes the matching of the appropriate labial or lingual surface of the tooth. The fixture may be rigid and of a material which can be changed to a non-rigid state upon application of a state-changing medium thereto. A secondary appliance, essentially like the fixture, may be formed over the fixture so as to be easily removed therefrom and from the bracket. Removal of the fixture, and, as appropriate, the appliance, from the bracket and shim is performed after the fixture with the bracket and shim mounted therein is assembled to a tooth and the bracket and shim are bonded thereto.

26 Claims, 13 Drawing Figures

ORTHODONTIC APPARATUS AND METHOD FOR TREATING MALOCCLUSION

This application is a further continuation-in-part of parent application Ser. No. 562,858, filed Dec. 19, 1983 now U.S. Pat. No. 4,526,540 issued July 2, 1985, and is copending with and a continuation-in-part of application Ser. No. 662,727, filed Oct. 19, 1984 now U.S. Pat. No. 4,557,096 issued 11/5/1985.

BACKGROUND OF THE INVENTION

1. Field of the Invention

The present invention relates to orthodontics and more particularly to a method and apparatus useful in precisely locating a bracket on a patient's tooth in optimal position, and more particularly to the convex nature of the bracket so utilized.

2. Description of the Prior Art

Prior art methods and apparatuses for precisely locating brackets on patient's teeth are disclosed in U.S. Pat. Nos. 3,738,005, 3,949,478, 4,014,096, 4,160,322, 4,183,141 and 4,360,341. Some of these patents disclose the use of procedures for the precise and correct placement of brackets upon the teeth utilizing idealized laboratory models. Brackets are mounted on the model in positions which conform to an idealized coplanar arch wire, while in others, prefabricated brackets are ideally located on the model and eventually incorporated into a transfer mask conforming to the malocclusion for placement on the patient's teeth. In still other of such patents, bracket holding devices are incorporated into transfer masks adapted to be registered over patient's teeth. The bracket-holding devices or portions thereof serve in locating the brackets on the teeth in positions corresponding to those selected on the model. In Cohen et al U.S. Pat. No. 3,738,005, there is disclosed the forming of a bracket-retaining mold which is of flexible, self-sustaining, resilient character that has been molded into positive, capturing engagement with the brackets. In following this procedure, one of the first steps is to make a dental cast of the patient's malocclusion. Brackets are applied to the tooth replicas by the orthodontist in desired locations. A bracket-retaining mold is formed over the dental cast having the brackets mounted thereon. This results in providing an arch shaped transfer device which is then used to carry the brackets to the patient's mouth where the brackets are bonded into position. The flexible transfer device or positioner is then flexed off the brackets and teeth leaving the brackets in place.

In Schinhammer U.S. Pat. No. 3,949,478, the procedure is similar to that just described except an idealized model is fabricated and brackets are removably secured to the tooth replicas in coplanar position. These replicas with mounted brackets are then removed from the model and placed in a jaw model of the patient's malocclusion. There is then formed an arch shaped mold or transfer device of elastic material for carrying the brackets to the patient's mouth. Since this mold is elastic, it may be peeled or flexed off the patient's teeth and brackets the same as described above.

In the Dellinger U.S. Pat. No. 4,360,341, an arrangement similar to that of the foregoing two patents is disclosed to the extent of using a flexible fixture or transfer device for applying the brackets to the teeth in the patient's mouth.

SUMMARY OF THE INVENTION

The present invention relates to orthodontic brackets having non-conforming surfaces of contact with teeth, adaptive shims associated therewith to provide a conforming mounting base, and apparatus and method by means of which such brackets and shims may be easily and precisely located and affixed to a patient's teeth in accordance with a fixed standard. In the context of the present discussion, the term "conforming" is intended to refer to a surface of a base portion of the bracket intended to be mounted to a patient's tooth or replica thereof, which surface has a topography substantially matching the surface anatomy of said tooth in the region of such mounting. The term "non-conforming" is intended to refer to a base portion of a bracket having a surface contour generally not matching any portion of the surface anatomy of any tooth. This standard may be customized as to a particular patient or established by one of a series of typical case setups. This invention finds particular utility in a technique in which the locus of slots of the brackets are predetermined on an idealized laboratory model, and are coplanar. When treatment of the patient is completed, the bracket slots are coplanar according to the slot arrangement on the idealized model. This result generally corresponds to prior art methods and apparatuses.

In one method of this invention, a non-conforming bracket is positioned on the patient's tooth precisely as predetermined according to the steps of forming a model for the patient's teeth in the shape of a dental arch with the replicas of the teeth ideally located. Each such non-conforming bracket has a contoured shim specially formed around the base portion thereof such that the region of contact between the base portion and the tooth in combination with a surface of the shim forms a conforming surface matching the surface anatomy of the tooth in the region of mounting. The shim also provides support to the base portion of the non-conforming bracket in order to maintain orientation of the bracket with respect to the tooth. Brackets and contoured shims are releasably mounted on selected replicas in preselected locations and at preselected orientations. A fixture of a formable material is formed over the dental arch into intimate conformity with the crowns, and the lingual and labial surfaces of the teeth replicas and onto the brackets and shims in securing engagement therewith. The fixture is formed of a material which after being formed is relatively rigid but can be subsequently altered as to its physical properties to facilitate removal thereof from the brackets as well as the patient's teeth.

The replica configuration of the fixture is utilized to locate and bond the bracket and shim onto the corresponding tooth in the patient's mouth. Once mounted, the physical properties of the utilized fixture are altered for facilitating removal thereof from the patient's teeth and the brackets and shims.

In a specific embodiment of the foregoing arrangement, the material of the fixture is biodegradable and is intimately conformed about a head portion of the bracket opposed to the base portion affixed to the replica, this material changing state into a non-rigid, flexible condition when subjected to moisture, which then presents little resistance to the practitioner in picking it off the patient's tooth and bracket.

Further features of the invention reside in the use of an adhesive for releasably securing the brackets and shims to the tooth replicas such that after the mold or fixture is formed over the replicas, the fixture and brackets and shims, as an integrated assembly, can be bodily snapped or released from the replicas in such a manner that the surface of the shim contiguous with the tooth retains substantially the precise surface contour thereof. When the bracket and its associated contoured shim are transferred to the patient's tooth, that same exposed surface will then essentially precisely match the corresponding desired attachment area on the tooth.

In a modified embodiment, after forming the arch shaped fixture on the ideal model as explained in the foregoing, a second fixture, which for convenience, is referred to as a secondary appliance, is formed thereover in intimate conformity with the crown, lingual, labial and bracket surfaces and in engagement therewith. This appliance is also of a moldable material which can either be identical to that of the first fixture or in the alternative of a non-rigid flexible plastic. The appliance is removed from the fixture without damaging it preferably by merely flexing it over the protrusions presented by the head portions of the brackets with the result being an arch shaped tray or appliance having a cavity conforming to the exterior shape of the idealized model with the fixture and brackets and shims mounted thereon.

The appliance is then divided or sectioned into replica units which can be utilized individually to mount brackets and shims in precise locations on the patient's teeth in precisely the same manner as the units formed of the primary fixture.

A still further alternative is to section the primary fixture into replica units after removing the fixture from the idealized model, these units having secured thereto the brackets and shims over which they were initially formed. These bracket-retaining units are then applied to the corresponding replicas of a previously cast maloccluded model of the patient's teeth. Some or all of such replicas may have such units applied thereto. Over this model is then formed a secondary fixture or appliance as explained hereinabove which intimately conforms to the maloccluded arch with the primary fixture units and brackets and shims thereon. The appliance may be secured to the fixture units either by means of a conventional, releasable adhesive or by reason of the physical embracement or encapsulation of the protruding bracket head portions of the first fixture. The appliance may then be manipulated to lift all of the fixture units with the retained brackets and shims from the maloccluded model and to transfer the same units directly to the patient's mouth where the brackets and shims will be engaged with the surfaces of the corresponding teeth as on the maloccluded model. Conventional techniques at this point may be employed for the purpose of bonding the brackets and shims directly to the teeth.

After the brackets and shims have been secured, the appliance may be flexed off the teeth and fixture units and the fixture units may then removed by altering the physical properties thereof as explained hereinabove. The brackets and shims are thus bonded to the respective teeth in the identical locations as were first established on the ideal and maloccluded models.

Instead of forming the secondary appliance over the entire dental arch, it may be formed over only partial arches depending upon the treatment being followed by the practitioner.

In each of the above identified aspects of the present invention, the primary object is to appropriately transfer a bracket or a group of brackets from an idealized replica of a dental arch to the patient's teeth in known positional relationships. Brackets, in accordance with the present invention, are provided with non-conforming surfaces at their respective base portions opposed to their respective bracket slots. Such non-conforming surfaces may be affixed to the maloccluded teeth at various preselected orientations in order to direct forces tending to cause rotation, tilting, etc., of the tooth, as well as its translation, thus enhancing the ability of the practitioner to correct a variety of such malocclusions.

It is an object of this invention to provide a method and apparatus which facilitates treatment of malocclusion.

It is another object of this invention to provide a method and apparatus for positioning non-conforming brackets onto teeth with a high degree of precision.

In another aspect of the invention, it is an object of this invention to provide a family of non-conforming brackets, useful in concert with the method and apparatus herein described, which brackets have non-conforming surfaces supported by shims affixable to labial or lingual surfaces of maloccluded teeth for directing translational, rotational, tilting, etc., forces upon said teeth as desired by the practitioner.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

In the drawings:

FIG. 7d presents an enlarged sectional view of the tooth contacting tip portion of the non-conforming bracket of FIG. 7a;

DESCRIPTION OF THE PREFERRED EMBODIMENT

In practicing the present invention, an idealized model of the patient's teeth is produced in accordance with conventional practice and otherwise as disclosed in Dellinger U.S. Pat. Nos. 4,014,096 and 4,360,341. A coplanar line or mark 12 is drawn on the tooth replicas 14. The line 12 on each replica 14 is utilized by the practitioner to select the desired location of the slot in a bracket, which bracket is to be directly bonded to the replica. The curvature of line 12 around the dental arch will correspond to the shape of an arch wire, preferably smoothly curvilinear and coplanar, to be used in the final stages of treatment. Other line patterns may be used without departing from the spirit and scope of this invention.

Suitable brackets 18 are bonded to the replicas 14 with the slots, for example, in registry with the line 12. While the bonding adhesive is conventional, it is of such character that it releasably mounts the bracket onto the replicas, adhering to the bracket more strongly than the replica. The adhesive in liquid o semi-liquid form is first applied to the attachment area on the labial or buccal surface of the replica, additional adhesive is provided on the mounting surface of the bracket base, following which the bracket is pressed onto the replica in the precise location desired and is held for a short period of time until the adhesive cures to the point at which it retains the bracket in place. Additional adhesive may be utilized to form a contoured shim between the non-conforming surface of the bracket and the surface of the replica. At this point, there will be excessive adhesive material which has flowed out from the edges of the bracket base, and this must be cleaned away. A suitably sharp instrument is used for the purpose, thereafter the adhesive is allowed to fully cure.

With the brackets so bonded to the replicas, a plastic cap or fixture 20 having the shape of the idealized model is formed over the replicas 14 and the brackets 18 mounted thereon. The fixture 20 intimately engages the incisal edges, the lingual surfaces and portions of the labial surfaces as indicated by the reference numerals 22, 24 and 26, respectively. The fixture thus has lingual, labial and incisal portions conforming to the surface anatomy of the corresponding portions of a patient's teeth. Further, the fixture 20 as molded over each bracket 18 (FIG. 3) intimately conforms to the undercuts and slots formed in the bracket head portions. This portion of the fixture 20, indicated by the numeral 28, appears as an embossment shaped substantially like the bracket head portion. In the portion 28, the material substantially encapsulates and captures the bracket 18 in position.

In a working embodiment, in which the material of the fixture 20 is a biodegradable film, a small amount of silicone adhesive is first applied to the labial surface of the bracket 18 for further adhering and locking the bracket 18 in place.

The material of the fixture 20 preferably is plastic and may be in liquid, semi-liquid or solid film form. In a preferred arrangement, this material is a solidified biodegradable film which is heat moldable to be vacuum formed over the replicas and brackets. After being so formed, the material hardens. Once hardened, the fixture is for all practical purposes rigid, the antithesis of being flexible, resilient or elastic.

Figure 5:
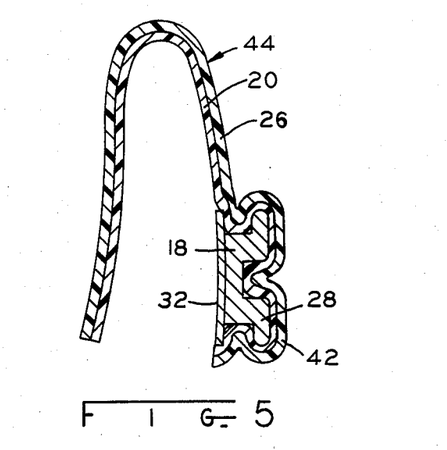
FIG. 5 is a sectional view like that of FIG. 3 of the fixture unit with the bracket attached just prior to being transferred to a patient's tooth.

The fixture 20 and the encapsulated brackets 18 now constitute an integrated assembly which is releasably adhered to the model replicas. After the various adhesives and materials have completely cured and hardened, the fixture-bracket assembly 18, 20 is merely withdrawn from the replicas simply by manually picking or forcing the brackets loose. Since the adhesive used is more releasable from the replica than it is the bracket, the adhesive will separate from the replica leaving an imprint on the exposed surface of the adhesive area which intimately conforms to that of the attaching surface of the replica, hence the patient's tooth. This adhesive then becomes a part of the bracket and serves as a contoured shim whereby the bracket may be intimately fitted to the corresponding patient's teeth. Once removed, the fixture-bracket assembly 18, 20 appears as shown in FIG. 5 (for a single tooth or replica) with the exposed surface 32 of the bracket base serving as an anatomical extension of the inner surface of the labial portion 26 of the fixture 20. The fixture 20 is quite rigid, and once removed from the replica, it will having interior shapes corresponding to that of the respective replicas.

At this point it is necessary to make certain that the surface 32 on the bracket base is chemically clean. This is accomplished by blasting with an inert gas, such as nitrogen to an extent as will clean the surface for bonding to a patient's tooth.

Figure 4:
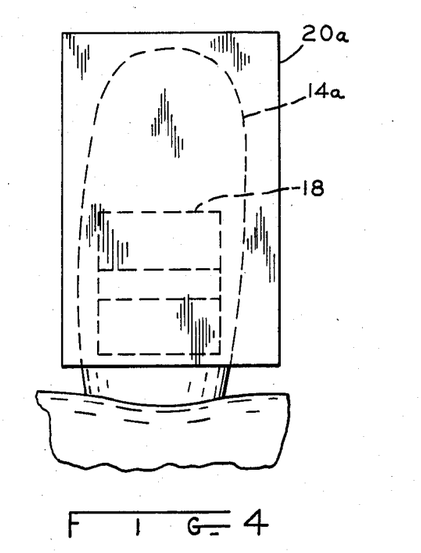
FIG. 4 is a labial view of the arrangement of FIG. 3.

The integrated arch-shaped fixture-bracket assembly 18, 20 is now sectioned into units, one for each replica 14. Each fixture unit 20a (see FIG. 4) may now be used to transfer a bracket 18 to the corresponding tooth 14a in the patient's mouth. The fixture 20a is now fitted over the corresponding tooth of the patient with the lingual, incisal and labial cavity portions fitting precisely, or in other words conforming to the surface anatomy of, the corresponding shape and irregularities of the tooth. Since the bracket 18 is positively oriented with respect to the fixture unit 20a, the bracket 18 will be positioned on the patient's tooth in precisely the same position as it was on the replica.

Bonding of the bracket to the tooth is accomplished by applying cement to the tooth or bracket base before the fixture unit is applied to the tooth. The fixture unit 20a is held in position until the cement cures. Since the fixture unit 20a is quite rigid, once the fixture is applied to the tooth, the bracket 18 is automatically and precisely positioned with respect to the tooth. Stated in other words, since the fixture 20a is not flexible, resilient nor elastic the fitting of the fixture 20a over the tooth does not result in undesired movement laterally or otherwise of the bracket 18.

Since the material of the fixture 20a completely encircles and grips the bracket 18, and since the material is relatively rigid, it is, for all practical purposes, essentially non-removable from the bracket 18. However, the material of the fixture 20a is so selected that it can be altered in its physical properties from, for example rigid to non-rigid, rigid to flexible, rigid to soft, etc. By making the fixture of a film of biodegradable material, subjecting the fixture while mounted in the patient's mouth and after the bracket 18 has become bonded to the tooth, to moisture such as the saliva in the patient's mouth or a spray of water, the fixture tends to soften, become pliable or flexible following which it may be simply manually picked off the bracket and thereby removed from the patient's tooth. Brackets are applied to all of the patient's teeth in the same manner, there being an individualized unit 20a for each tooth.

Figure 6:
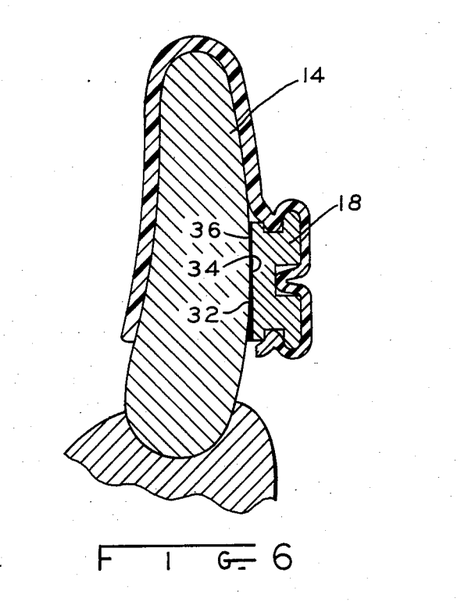
FIG. 6 is a view similar to that of FIG. 3 illustrating in exaggerated form the method of shimming and conforming the base of a substantially conforming bracket to an attachment area on the patient's tooth.

Further exemplification of the temporary attachment of the bracket 18 to the replica 14 and the formation of a contoured shim is illustrated in FIG. 6. In this figure the bottom surface 34 of the bracket 18 is shown to be shaped somewhat reversely with respect to the tooth surface. The adhesive is indicated by the numeral 36 as filling the space between the bracket and the replica. Once the adhesive hardens, a surface like the surface 32 remains which will conform to the corresponding portion of the patient's tooth. The reversely shaped surface 34 permits use of the same bracket for mounting on teeth of almost all surface contours, the adhesive serving as a filler for completing the shaping of the bracket base for fitting the patient's tooth.

The biodegradable film used in a working embodiment of this invention is essentially a flat sheet or film which is self-supporting and preferably square in shape. The material of the film is polyvinylalchohol, for example. It measures four inches on a side and is approximately eight to twelve mils thick. It may be used in conventional vacuum-forming equipment wherein heat is applied to the film at the time it is being vacuum formed over the replicas. Other materials may, of course, be used so long as the finished fixture is relatively rigid and can be altered in its physical properties from a rigid condition to one that is pliant, flexible or in other words non-rigid so that it may be conveniently and easily removed from the bracket once the bracket has been mounted on the patient's tooth.

The individualized fixtures 20a are light in weight, diminutive, and non-bulky thereby facilitating manipulation for quick, easy, accurate installation. By being rigid the fixture enables direct bonding in a precise pre-selected position which, in utilizing the preferred technique described earlier, permits finished treatment by means of a pre-configured, coplanar archwire. Since the fixtures 20a are individualized, one for each tooth, they are individually useable irrespective of any anatomical changes as to other teeth. This is better understood by comparing with known positioners which are arch shaped to fit a patient's total malocclusion (See Cohen et al U.S. Pat. No. 3,738,005 and Shinhammmer U.S. Pat. No. 3,949,478). Any change in any one tooth, for example, as to position, size, etc., renders the positioner unuseable since it no longer fits the one tooth hence it cannot fit over the remaining teeth.

Figure 1:
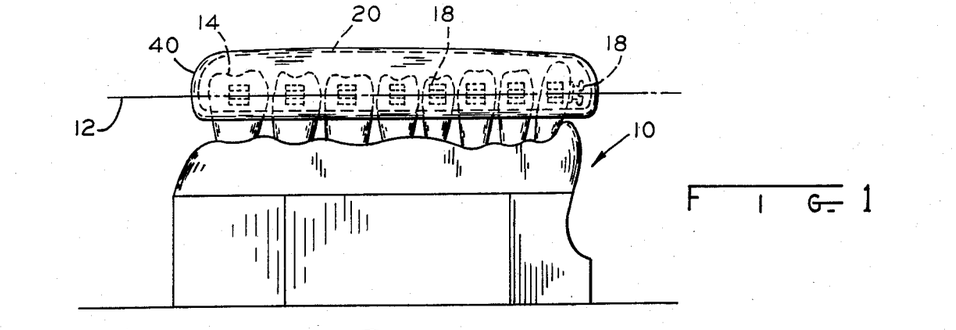
FIG. 1 is a side elevation of an idealized model of a dental arch illustrating one portion of the method of this invention.
Figure 2:
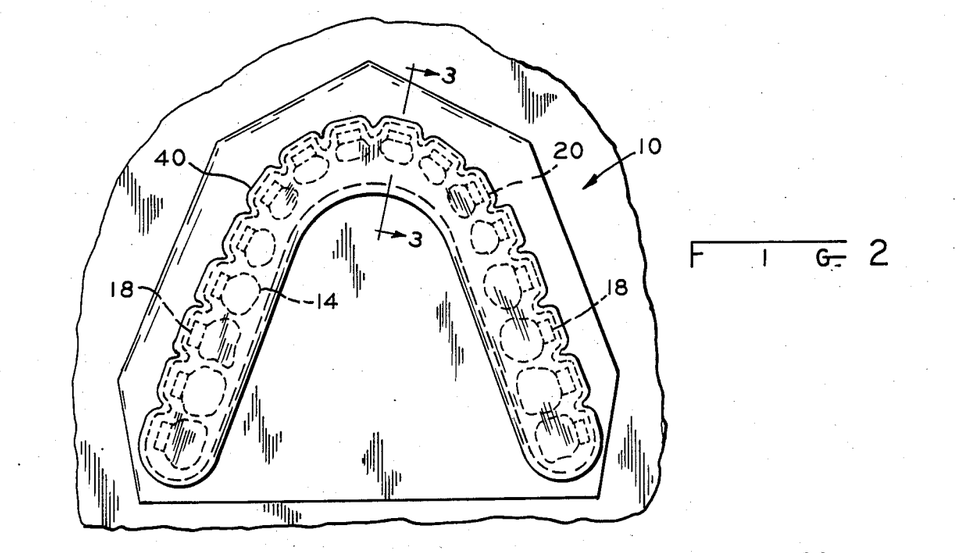
FIG. 2 is a top plan view thereof.

A variation or implementation of the foregoing method and apparatus is provided in accordance with the following. Referring to FIGS. 1 and 2, the primary fixture 20 is shown in dashed lines. Once this primary fixture 20 has been formed, a secondary occlusal fixture or overlay, also referred to as a secondary appliance, is formed thereover, as indicated by the numeral 40. The method and material employed may be identical to that disclosed hereinbefore, or in the alternative, a material which in the final anaylsis is suitably flexible, such as a type of vinyl plastic or the like, may be utilized. The method and materials used are such that the secondary appliance 40 can be physically separated from the fixture 20 simply by flexing the appliance 40 thereoff. If desired, a suitable releasable adhesive may be employed for securing both the fixture and appliance 20, 40 together for purposes of handling.

Figure 3:
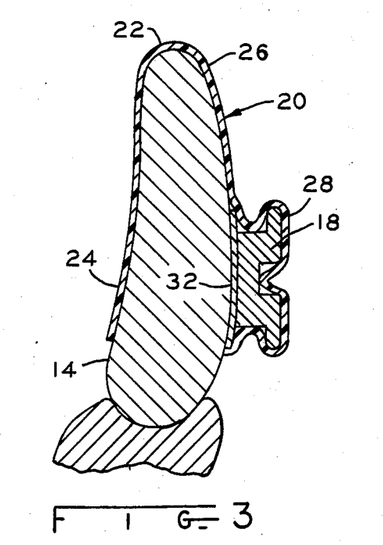
FIG. 3 is an enlarged sectional view taken substantially along section line 3—3 of FIG. 2.

Substantially in accordance with the method explained hereinbefore, the fixture-appliance assembly 18, 20, 40 is merely withdrawn from the model by manually picking or forcing the brackets loose. As removed, the fixture-appliance assembly, 18, 20, 40 appears as shown in FIG. 5 (for a single tooth or replica) with all the other features remaining the same as already explained. At this point, the fixture-appliance 20, 40 as an assembly is sectioned into units, one for each replica 14. Alternatively, the appliance 40 can be peeled off the underlying fixture 20 then the appliance 40 sectioned into units. In vacuum forming or molding the appliance 40 in conformity with the external shape of the fixture-bracket 18, 20 assembly, the appliance will have formed therein sockets or cavities 42 having shapes corresponding to the embossments 28 (FIGS. 3 and 5). By making the material of the fixture 20 suitably thin, the cavity 42 can be made to correspond substantially to the shape of the head of the bracket as shown in FIG. 6, whereby a sectioned appliance unit 44 can have fitted and captured thereinto a bracket 18 which bracket now may be transferred directly to the patient's tooth according to the same procedure explained in the foregoing and using a fixture unit 20. This procedure would be employed primarily for the purpose of replacing brackets which have for some reason become dislodged from the patient's tooth. After using the appliance unit 44 to rebond a bracket 18, the unit 44 can be reused in the future provided it is made from a material that is flexible and is not alterable in its physical properies from the mere application, for example, of moisture or saliva in contrast with the case of the fixture 20.

With reference to FIGS. 6 and 7 through 10, the bracket 18 incorporated in the preceding descriptions, as exemplified in FIG. 6, is envisioned to have a primary embodiment wherein such a bracket, at the region of contact between the bracket and the tooth or replica, has a non-conforming shape. FIG. 7a illustrates a first form of a bracket 61 wherein the base has a very short radius of curvature, approaching a point 62, which may be further observed in the enlargement of FIG. 7d. A moderate radius of curvature, represented by the bracket 63 of FIG. 7b, is advantageous in particular utilizations, as will become more clear below. FIG. 7c illustrates a bracket 64 having a large radius of curvature, which, in one extreme, may approach the illustrated bracket 18 of FIGS. 3 through 6.

Figure 7A:
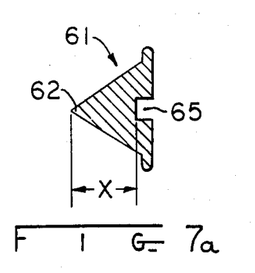
FIGS. 7a, 7b and 7c illustrate sectional views of brackets having, respectively, differing shaped non-conforming base surfaces in accordance with the present invention.
Figure 7B:
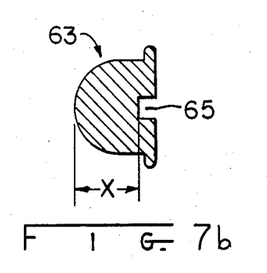
Figure 7C:
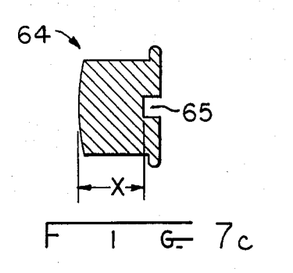
Figure 7D:
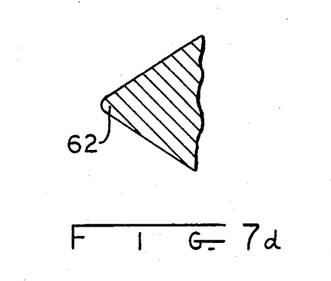

Each of the brackets 61, 63 or 64 illustrated in FIGS. 7a, 7b or 7c, respectively, enjoys a common characteristic in that a stand off distance "x", from a region of primary contact with a tooth or replica, to a slot 65 formed to receive the aforesaid arch wire, is substantially the same. Moreover, either of the brackets 61, 63 or 64 may be oriented at a small angle with respect to the tooth or replica, with the distance from the slot to the point of contact remaining substantially unchanged. This allows the practitioner to intentionally incorporate an angle of tilt or an offset with respect to the tooth during attachment of the bracket to the replica, thereby enabling controlled direction of force upon the tooth from a smooothly curvilinear coplanar arch wire so as to tend to correct tilted or axially rotated malocclusions. Additionally, the relative invariance of the stand off distance reduces the positioning constraints imposed upon the practitioner by earlier known methods and apparatus, thereby providing a basis for a reduction in time expenditure of the practitioner and, alternatively, facilitating robotic placement of the brackets on the replicas.

By providing a practitioner with a family of brackets 61, 63 and 64, having a number of discrete stand off distances, treatment of a significant malocclusion may be accomplished by using a single fixture or appliance. This allows infinite in-out (buccal-lingual) adjustment. Also, as the malocclusion is reduced, another bracket of the same type 61, 63 or 64, having a differing, generally greater, stand off distance, may be substituted without removal of brackets from adjacent teeth or significant change in the form or positioning of the arch wire.

Figure 8:
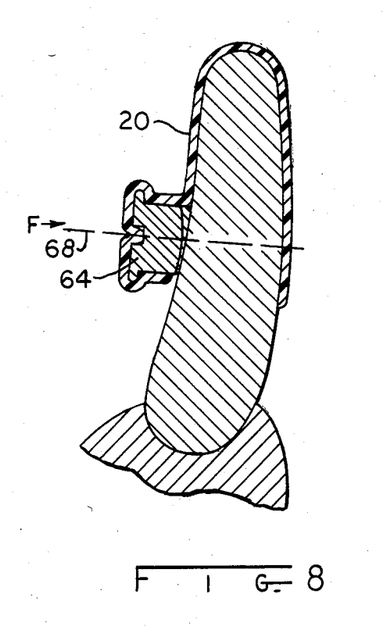
FIG. 8 is a sectional view like that of FIG. 3 but with a non-conforming bracket and contoured shim disposed in contact with the lingual surface of a tooth replica.

The brackets 61, 63 and 64 are appropriately incorporated into the above-described methods in like manner as has been set forth for brackets 18 of FIGS. 3 and 6. After forming an appropriate replica of the patient's dental arch, selected brackets 61, 63 or 64, each having a desired stand off distance so as to establish the locus of the slots 65 to fall along a smoothly curvilinear coplanar arch wire position, are respectively attached to the replica teeth by using the adhesive previously described. Each such bracket 61, 63 or 64, respectively, is in attachment, oriented in angle and position so as to provide the desired tilt and/or rotation as well as the heretofore understood translation for correction of the malocclusion. Additional adhesive material (see FIG. 6) is added to form a contoured shim, as has been previously set forth. In the use of brackets 61, 63 or 64, the formation of such a shim also provides a larger surface of contact between the bracket and the tooth replica as well as enhanced structural integrity of the position bonding of the bracket to the tooth replica. As in the previously described method, the contoured shim thus formed will, in general, conform to the individual tooth surface irregularities to facilitate proper bracket and shim placement upon transfer to the patient's tooth. When the appropriate brackets have been mounted to the replica dental arch, a fixture is formed to substantially encapsulate the bracket, shim and exposed surfaces of the replica dental arch. The brackets may then be transferred to the patient's teeth as has been previously described, either directly, or with the utilization of a secondary appliance. FIG. 8 illustrates a cross-section of a bracket 64 attached to a lingual surface of a replica tooth and includes the formation of the fixture 20. A bracket 18, 61 or 63 may be substituted for the illustrated bracket 64, within the discretion of the practitioner.

Figure 9:
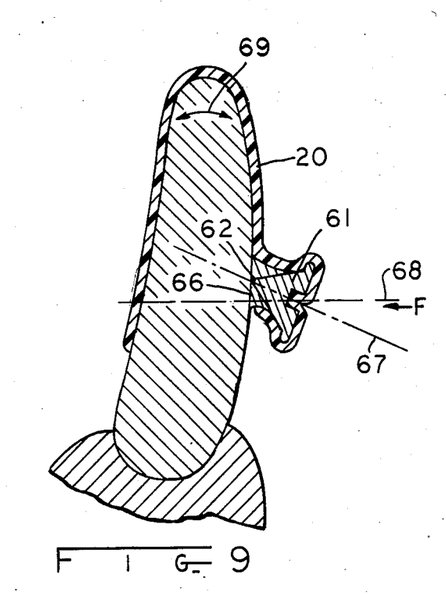
FIG. 9 is a sectional view like that of FIG. 3, illustrating the attachment of a non-conforming bracket and shim contoured in accordance with the present invention at an angularly offset orientation, exaggerated for clarity, wherein a force tending to tilt a tooth may be imposed.

FIG. 9 presents an angularly exaggerated cross-sectional view indicating the manner in which a bracket 61 may be mounted so as to induce tilting of a maloccluded tooth. By tilting the axis of symmetry 67 of the bracket 61 with respect to the plane 68 of the arch wire, thereby offsetting vertically the point of attachment of the point 62 of the bracket 61 to the tooth replica, and then forming the contoured shim 66, the force F exerted on the bracket by the arch wire, generally directed in the plane 68, will produce a resulting moment about the point 62, thereby tending to tilt the tooth in the appropriate direction indicated by the arrows 69. Thus, in addition to any translation of the tooth in the plane 68, the vertical orientation of such a malocclusion may be varied. Either of the brackets 18, 63 or 64 may be utilized in lieu of the illustrated bracket 61 for this purpose, as may be appropriate.

Figure 10:
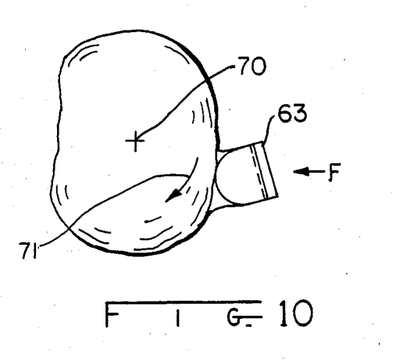
FIG. 10 is a plan sectional view of a tooth replica illustrating the attachment of a non-conforming bracket and shim contoured in accordance with the present invention at an angularly and positionally offset orientation, exaggerated for clarity, wherein a force tending to rotate a tooth may be imposed.

Referring next to FIG. 10, a top view of a tooth having, by way of example, a bracket 63 attached thereby by a contoured shim 66, illustrates the attachment of such a bracket in an offset and slightly tilted orientation in order to effect a rotation of such a maloccluded tooth. In the alternative, either a bracket 18, a bracket 61 or a bracket 64 may be utilized, with similar effect. By exaggerating the angular positioning orientation in the plane of the arch wire, it may be clearly seen that such positioning and orientation of of the bracket 63 will transmit the force F from the arch wire to the tooth in a manner tending to cause the tooth to rotate about its center of mass 70.

Since the bracket-locating fixtures of this invention are custom fabricated for the individual patient, and since the non-conforming shape of the tooth contacting surface of the bracket removes much of the positioning accuracy requirements placed on the practitioner, free hand placement of the bracket on the patient's tooth and many of the judgment factors involved on the part of practitioner are eliminated. Accuracy in bonding location and orientation coupled with a savings in practitioner's time can indeed provide for improved treatment at lower costs.

Summarizing, the invention broadly involves transporting the prepositioned and appropriately oriented bracket having a non-conforming base and having an associated contoured shim to the mouth by means of a relatively rigid or non-rigid fixture or appliance, bonding the bracket and shim in place, and then in the case of the rigid fixture altering the properties from rigid to flexible, to facilitate removal from the bracket. Ideal and maloccluded models of the patient's teeth may alternatively be used for making (1) duplicate transfer units for both initial and replacement installations of brackets and shims having differing standoff distances on individual, single teeth of a patient and (2) arch-shaped appliances for precisely locating and installing simultaneously a plurality of brackets and shims on patient's teeth.

While there have been described above the principles of this invention in connection with specific apparatus, it is to be clearly understood that this description is made only by way of example and not as a limitation to the scope of the invention.

What is claimed is:

1. The method of fabricating an orthodontic appliance and repositioning a patient's teeth, comprising the steps of:
    forming a model of the patient's teeth in the shape of a dental arch with replicas of the teeth ideally located;
    releaseably mounting brackets on selected replicas in preselected locations, said mounting being accomplished by use of an adhesive which adheres to the brackets with more force than to the replicas, said brackets each having a base portion for mounting to said replicas, said base portion providing a mounting surface that does not conform to the contour of the surface anatomy of the replica in the area of attachment;
    allowing said adhesive to fill the gaps and spaces formed between each such base portion and its associated replica, thereby forming a contoured shim conforming to the contours of the surface anatomy of the replica, said adhesive further being of such character as to solidify and, when desired, to separate from said replica flush with such conforming area, thereby leaving the remainder of the adhesive secured to the base portion of the bracket;

forming a fixture over the dental arch model in intimate conformity with the respective replica crowns, lingual and labial surfaces and onto said brackets and contoured shims in securing engagement with said brackets and contoured shims, said fixture being formed of a material which, after being formed, is relatively rigid and in that state not readily removable from said brackets and contoured shims but which material can be subsequently altered as to its physical properties to facilitate removal thereof from said brackets and contoured shims;

removing the thus formed fixture-bracket-shim assembly from the model as a single unit by utilizing the differential in the adhering character of the adhesive to separate said adhesive from the replicas;

utilizing replica portions of said fixture-bracket-shim assembly to locate and bond the respective brackets and contoured shims onto the corresponding teeth in the patient's mouth, said contoured shim forming a surface which precisely fits the corresponding area on the tooth in the patient's mouth; and altering the physical properties of the utilized fixture portions while in the patient's mouth for removal from the patient's teeth and said brackets and contoured shims.

2. The method of claim 1 including the step of cleaning the exposed surface of the contoured shim after separation from the replica and prior to installation in the patient's mouth.

3. The method of fabricating an orthodontic device for re-positioning a patient's teeth, comprising the steps of:

forming a model of the patient's teeth in the shape of a dental arch with the replicas of the teeth ideally located;

releaseably mounting non-conforming brackets, at their respective base portion surfaces, on selected replicas in preselected locations and orientations, said mounting being accomplished by use of an adhesive which adheres to the brackets with more force than to the replicas, each bracket having a slot formed therein on a surface opposite a centroid of the non-conforming base portion thereof, said slots to be generally disposed along a smoothly curvilinear coplanar locus, conforming to and spaced from, the dental arch;

forming a contoured shim associated with each bracket by allowing said adhesive to fill the gaps and spaces formed between each such non-conforming base portion and its associated replica, said adhesive further being of a character as to solidity and, when desired, to separate from said replica flush with, and conforming to, the contours of the surface anatomy of the replica in the region of attachment;

forming a fixture over the dental arch in intimate conformity with the respective replica crowns, lingual and labial surfaces and onto said brackets and shims in securing engagement with the brackets and shims, said fixture being formed of a material which after being formed, attains a relatively rigid state and in which state said fixture is not readily removable from said brackets and shims, said material further having a characteristic that it can be subsequently altered as to its physical properties to facilitate removal from said brackets and shims;

removing the thus formed fixture-bracket-shim assembly from the model as a single unit;

dividing replica portions of said fixture-bracket-shim assembly into fixture units, one for each selected replica, the fixture units corresponding to said selected replicas and having said brackets and shims secured therein;

forming a maloccluded model of the patient's teeth;

fitting the bracket and shim bearing fixture units over the corresponding replicas of the maloccluded model;

forming a secondary fixture-retaining and transferring appliance over the maloccluded model in intimate conformity therewith and in securing engagement with said bracket and shim bearing fixture units;

removing the secondary appliance and the therein secured bracket and shim bearing fixture units as an integrated assembly from the maloccluded model;

applying said integrated appliance to the patient's teeth to locate and secure the brackets and contoured shims to the respective teeth; and removing the appliance and the fixture units from the teeth, including altering the physical properties of the fixture units while in the patient's mouth for their removal from the teeth.

4. The method of claim 3 including forming said appliance of a material which is flexible; said removing step including flexing said appliance as necessary to remove it from said bracket and shim bearing fixture units, after installation in the patient's mouth, thereby leaving the latter in position on the patient's teeth, then removing said fixture units by the aforesaid step of altering the physical properties thereof.

5. The method of claim 4 wherein said bracket and shim bearing fixture units have an embossed portion overlying and corresponding to the shape of the retained brackets and shims, the forming of said appliance including intimately conforming the same to said embossed portion thereby tending to lock said units thereto.

6. The method of claim 5 wherein the material of said fixture is biodegradable such that upon the application of moisture said material becomes less rigid and thereby removable from said brackets, shims and teeth.

7. The method of claim 3 wherein the steps of forming said fixture and of forming said appliance each includes the vacuum forming of relatively thin sheets of material onto the respective models.

8. The method of claim 3 including forming said appliance of a material having substantially the same properties as those of said fixture units.

9. The method of claim 8 wherein the step of removing the appliance and the fixture units from the patient's teeth include altering the physical properties of both said appliance and fixture units.

10. The method of claim 8 wherein the material of both said fixutre units and said appliance is biodegradable.

11. Apparatus for treating malocclusions comprising: at least one bracket having a head portion and a base portion, wherein said head portion includes a slot adapted to receive a conventional orthodontic dental arch wire and said base portion provides a surface for attaching the bracket to a selected patient's tooth, which surface is generally non-conforming to the surface anatomy of said tooth in the region of attachment;

a contoured shim, formed substantially around said non-conforming base portion of said bracket out of a solidifying adhesive material so as to orient said bracket angularly and positionally with respect to said patient's tooth, said shim and said base portion providing, in combination, a surface substantially conforming to the surface anatomy of the corresponding portion of the selected patient's tooth, said adhesive material having a further character that it adheres more strongly to said bracket than to said tooth;

a locating fixture having an internal cavity provided with lingual and labial sides and an incisal crown portion therebetween, said lingual side, incisal crown portion and said labial side conforming to the surface anatomy of the corresponding portions of the selected patient's tooth, said internal cavity including a first portion of either said labial or lingual side having an embossment formed therein to fixedly embrace the head portion of said bracket in said angular and positional orientation with respect to the selected patient's tooth, said fixture further being formed of a relatively thin sheet-like material of substantially uniform thickness which can be changed in physical properties to become relatively rigid after formation about said selected patient's tooth and said bracket and shim and to become removably pliant upon application thereto of a property-changing medium; and a secondary transfer appliance of pliantly deformable sheet-like material overlying said fixture bearing said bracket and shim in intimate conformity therewith, said appliance having a cavity portion which receives said embossment of said fixture, said cavity being of a size and shape to engage and retain said head portion of said bracket.

12. The apparatus of claim 11 wherein said appliance is self-supporting and flexible so as to enable it to be deformed for removal from said fixture and embossment.

13. The apparatus of claim 11 wherein said appliance is formed of material having substantially the same physical properties as said fixture.

14. The apparatus of claim 13 wherein said fixture and said appliance are each of a biodegradable material.

15. Apparatus for positioning brackets onto a patient's teeth comprising:

a plurality of individual locating fixtures having internal cavities provided with lingual and labial sides and incisal crown portions, respectively, said lingual sides, incisal crown portions and labial sides, respectively, conforming to the surface anatomies of the corresponding portions of selected ones of the patient's teeth, said fixtures being relatively rigid and further of a material which can be changed in physical properties upon application of a property-changing medium thereto;

a plurality of brackets each having head and base portions, portions of either said labial or lingual sides of said fixtures fixedly embracing the head portions of said brackets in such positions as to angularly and positionally orient said base portions in substantially the same anatomical surfaces as the respective labial or lingual sides, respectively, said base portions being generally non-conforming to said anatomical surfaces, conformance therewith arising from contoured shims of a solidified adhesive material adhering to said non-conforming base portions, said shims having formed thereon conforming surfaces respectively matching said teeth; and a fixture-integrating and retaining appliance having internal cavities arranged and conforming to the patient's malocclusion with said fixtures bearing said brackets and shims fitting onto said selected teeth thereof, said appliance being removably secured to and integrating said fixtures in place, whereby said appliance with said fixtures secured in place may be conformably engaged with the patient's teeth thereby selectively locating said fixtures bearing said brackets and shims onto the selected teeth in the patient's mouth.

16. The apparatus of claim 15 wherein the one of said lingual or labial sides of said fixtures which embraces the respective bracket head portions is relatively thin and of uniform thickness, the portion of said one side of each fixture which overlies the respective head portion of the bracket consisting of an embossment of conforming shape, and wherein said appliance is of a flexible material having cavities formed therein which removably capture said bracket head portion enclosing embossments of said fixtures, respectively, thereby contributing to the securement and integration of said fixtures to said appliance.

17. The apparatus of claim 15 wherein the one of said lingual or labial sides of said fixtures which embrace the respective bracket head portions is relatively thin and of uniform thickness, the portion of said one side of each fixture which overlies the respective head portion constituting an embossment of conforming shape, said appliance being of a material having properties substantially like the material of said fixtures and having cavities which removably capture said embossments, respectively, thereby contributing to the securement of said fixtures to said appliance.

18. The apparatus of claim 17 wherein the material of said fixtures and said appliance is biodegradable.

19. A method of fabricating an orthodontic device for re-positioning a patient's teeth, comprising the steps of:

forming a model of the patient's teeth, each of the patient's teeth being represented by a replica, said model being in the shape of a dental arch with the replicas of the teeth ideally located;

releaseably mounting brackets having non-conforming base portions and head portions onto selected replicas such that said base portions are in preselected angular and positional orientations, while said head portions are aligned along a substantially smoothly curvilinear coplanar locus;

forming a contoured shim surrounding each of said non-conforming base portions, respectively, each said contoured shim conforming with the surface anatomy of the portion of the replica tooth proximate to the point of attachment of the respective bracket, said shim being releasably attached to the replica surface during formation thereof, and rigidly attached to the base portion of its respective bracket;

forming a fixture over the dental arch in intimate conformity with the respective incisal crown, lingual and labial surfaces of the replicas and onto the head portions of said brackets in securing engagement with the latter, said fixture being formed of a material which after being formed is relatively rigid and in that state not readily removable from said brackets and shims but which can be subsequently altered as to its physical properties to facilitate removal thereof from said brackets and shims, said fixture being relatively thin and of a substantially uniform thickness, the portions thereof overlying the head portions of said brackets thereby being in the form of embossments conforming to the shapes of the head portions, respectively;

forming a secondary appliance over said model with said fixture in place on the selected replicas into intimate conformity therewith and in capturing engagement with said embossments; and dividing replica portions of said secondary appliance into units, one for each fixture mounted replica tooth, each unit thereby having a cavity conforming to the lingual, labial, incisal and embossment portions of the respective fixture mounted replica, the embossment cavity portion being formed to a size and shape as will position and retain the head portion of the corresponding bracket and shim in essentially the same relative position and orientation as that established on the corresponding replica, whereby each unit of the secondary appliance can be used to locate and bond the respective bracket and shim onto the corresponding tooth in the patient's mouth.

20. The method of claim 19, including a step wherein said fixture is divided in the same manner as said appliance to provide bracket and shim-carrying fixture units, said bracket and shim-carrying fixture units being utilizable to locate and bond respective brackets and shims onto the corresponding teeth in a patient's mouth.

21. The method of claim 19 wherein said appliance is formed of flexible material, and including the further step of releaseably adhering each bracket and shim into its respective embossment cavity.

22. The method of claim 19 wherein both said fixture and, said appliance are formed of biodegradable material, and including the further step of applying an appropriate medium to cause the biodegradation of removal of said fixture and said appliance subsequently to the bonding of the respective brackets and shims onto the corresponding teeth in the patient's mouth.

23. A non-conforming bracket for use in orthodontic correction of malocclusion, comprising an integral body having a base portion and a head portion axially obverse thereto, wherein said base portion is formed to have a generally convex surface adapted to be affixed to a tooth or replica at substantially a single point of contact therebetween, and said head portion is formed to have a substantially planar surface orthogonally situated with respect to an axis of the bracket and opposed to a central point of said surface said base portion, said planar surface having a slot formed therein normal to the axis of said bracket, said slot having a bottom axially separated from said central point of said surface of said base portion by a preselected stand-off distance through said integral body, said convex surface of said base portion having a radius of curvature at least equal to said stand-off distance.

24. The bracket of claim 23, wherein said surface of said base portion surface has a radius of curvature substantially equal to said stand-off distance.

25. The bracket of claim 23, wherein said surface of said base portion surface has a radius of curvature greater than said stand-off distance.

26. The bracket of claim 23, further comprising a contoured shim formed external of, and substantially surrounding, said base portion and rigidly affixed thereto, said shim and said point of contact of said base portion to a tooth integrally forming a surface conforming to the surface anatomy of said tooth in the region of attachment between said tooth and said combined conforming surface.

* * * * *